United States Patent
Katayama et al.

(10) Patent No.: US 10,544,170 B2
(45) Date of Patent: Jan. 28, 2020

(54) ORGANOSILICON COMPOUND AND METHOD FOR PRODUCING SAME

(71) Applicant: Shin-Etsu Chemical Co., Ltd., Tokyo (JP)

(72) Inventors: Taiki Katayama, Annaka (JP); Isao Iwasaki, Annaka (JP); Takafumi Sakamoto, Annaka (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 0 days.

(21) Appl. No.: 16/083,214

(22) PCT Filed: Mar. 8, 2017

(86) PCT No.: PCT/JP2017/009265
§ 371 (c)(1),
(2) Date: Sep. 7, 2018

(87) PCT Pub. No.: WO2017/183347
PCT Pub. Date: Oct. 26, 2017

(65) Prior Publication Data
US 2019/0085002 A1   Mar. 21, 2019

(30) Foreign Application Priority Data

Apr. 19, 2016 (JP) .................. 2016-083625

(51) Int. Cl.
*C07F 7/18* (2006.01)
*C08K 5/5419* (2006.01)
*C07B 61/00* (2006.01)

(52) U.S. Cl.
CPC .............. *C07F 7/1804* (2013.01); *C07F 7/18* (2013.01); *C07F 7/188* (2013.01); *C08K 5/5419* (2013.01); *C07B 61/00* (2013.01)

(58) Field of Classification Search
CPC .......... C07F 7/18; C07F 7/1804; C07F 7/188; C08K 5/5419
See application file for complete search history.

(56) References Cited

U.S. PATENT DOCUMENTS

| | | | |
|---|---|---|---|
| 5,417,216 A | 5/1995 | Tanaka | |
| 5,510,481 A | 4/1996 | Bednarski et al. | |
| 2007/0077782 A1* | 4/2007 | Lee | H01L 21/02063 438/781 |
| 2010/0130658 A1 | 5/2010 | Iwasaki et al. | |

FOREIGN PATENT DOCUMENTS

| | | |
|---|---|---|
| JP | 39-27643 | 12/1964 |
| JP | 55-43119 A | 3/1980 |
| JP | 62-42993 A | 2/1987 |
| JP | 7-39547 A | 2/1995 |
| JP | 2011-51926 A | 3/2011 |
| JP | 4775600 B2 | 9/2011 |
| JP | 2013-35768 A | 2/2013 |

OTHER PUBLICATIONS

Clive et al., "[2.2.1]-Bicyclic systems releveant to synthetic studies on CP-225,917-use of a new silylated cyclopentadiene," Tetrahedron 60(2004) 4205-4221. (Year: 2004).*
Clive et al., Tetrahedron, 60 (2004), 4205-4221. (Year: 2004).*
Getmanova et al., "Diphilic carbosilane dendrimers with different densities of the hydrophilic layer", Russian Chemical Bulletin, Int'l Edition, 2004, vol. 53, No. 1, pp. 137-143.
Getmanova et al., "Polyhydroxycarbosilanes of dendritic structure", Reactive & Functional Polymers, 1997, vol. 33, pp. 289-297.
International Search Report, issued in PCT/JP2017/009265, dated May 9, 2017.
Makarova et al., "Reactions of cage metal siloxanes with functionalized organochlorosilanes", Russian Chemical Bulletin, Int'l Edition, 2003 ,vol. 52, No. 1, pp. 170-172.
Tucker-Schwartz et al., "Thiol-ene Click Reaction as a General Route to Functional Trialkoxysilanes for Surface Coating Applications", Journal of the American Chemical Society, 2011, vol. 133, pp. 11026-11029.
Written Opinion of the International Searching Authority, issued in PCT/JP2017/009265, dated May 9, 2017.
Zhdanov et al., "Reactions of 1,4-dioxa-2-silacyclohexanes with acetyl chloride", Russian Chemical Bulletin, 1998, vol. 47, No. 12, pp. 2445-2447.
Japanese Office Action for Appl. No. 2018-513059 dated Jul. 23, 2019 (w/ English translation).
Extended European Search Report dated Oct. 24, 2019 for Application No. 17785690.3.

* cited by examiner

*Primary Examiner* — Clinton A Brooks
*Assistant Examiner* — Kofi Adzamli
(74) *Attorney, Agent, or Firm* — Birch, Stewart, Kolasch & Birch, LLP

(57) ABSTRACT

Provided are an organosilicon compound capable of improving the storage stability of a composition (curability after long-term storage); and a method for producing the same. The organosilicon compound has, in one molecule, at least one carboxylic acid ester group represented by the following general formula (1) and at least one hydrolyzable silyl group represented by the following general formula (2):

$$-OC(=O)CH_2R_1 \qquad (1)$$

wherein $R^1$ represents a hydrogen atom or a methyl group;

$$-SiR^2{}_{3-n}Y_n \qquad (2)$$

wherein $R^2$ represents a substituted or unsubstituted monovalent hydrocarbon group having 1 to 12 carbon atoms, Y represents a hydrolyzable group, and n represents an integer satisfying $1 \le n \le 3$.

14 Claims, No Drawings

ORGANOSILICON COMPOUND AND METHOD FOR PRODUCING SAME

TECHNICAL FIELD

The present invention relates to a novel organosilicon compound, particularly to an organosilicon compound capable of improving the storage stability of an organopolysiloxane-containing room temperature-curable organopolysiloxane composition; and a method for producing the same.

BACKGROUND ART

Conventionally, among organopolysiloxane compositions that are turned into rubbery elastic bodies when cured at room temperature, the so-called one-component type (one-component) room temperature-curable organopolysiloxane composition allowing curing reaction to progress when in contact with water in the air has been widely used as an elastic adhesive agent and coating material in the electrical/electronic industry or other industries, or as an architectural sealing material, for example. This is because there are required no cumbersome steps of weighing and mixing a base polymer, a cross-linking material, a catalyst or the like immediately before use, which causes no error in composition; and because an excellent adhesiveness to a wide range of base materials is usually exhibited even when no primer is employed. Such one-component type room temperature-curable organopolysiloxane composition is often categorized by a compound(s) released therefrom when coming into contact with water in the air, typical examples of which include organopolysiloxane compositions of a deacetic acid type, a deoximation type, a deamide type, a dehydroxylamine type, a deacetone type, and a dealcoholization type. Among these examples, an dealcoholization-type organopolysiloxane composition which is curable by releasing an alcohol(s) is particularly preferred and used, because it has little odor, does not corrode metals such as copper and iron, and exhibits an excellent self-adhesiveness (adhesiveness to various base materials after curing, when no primer is employed) and adhesion durability.

However, although a one-component dealcoholization-type organopolysiloxane composition has the above excellent properties during a short period of time after its production, the composition has a flaw(s) in its storage stability where, for example, the properties that are observed immediately after the production of the composition may be lost over time during storage, depending on the ingredients of the composition. Further, when stored under direct sunlight at the site of use, or when stored in a container while being transported, the storage environment is often a high temperature environment of a temperature greater than 50° C. Thus, there has been a problem that, for example, not only the properties that are observed immediately after production may be lost even after a relatively short-term storage, but curing failures may occur as well.

The one-component dealcoholization-type organopolysiloxane composition has long been proposed. Typical examples of such composition include a composition comprised of a hydroxyl group end-capped organopolysiloxane, alkoxysilane and a titanium compound, as disclosed in Japanese Examined Patent Application Publication No. Sho 39-27643 (Patent document 1). Further, JP-A-Sho 55-43119 (Patent document 2) discloses a composition comprised of an organopolysiloxane having an alkoxysiloxy group at its end, alkoxysilane and alkoxytitanium. However, these compositions have exhibited a problem that, for example, when calcium carbonate is added to impart a favorable physical property to a sealing material, the storage stability of the compositions may be impaired in a way such that a desired property may not be achieved after a long-term storage, and/or the compositions may fail to cure after being stored in a high-temperature environment of a temperature higher than 50° C. Moreover, Japanese Examined Patent Application Publication No. Hei 7-39547 (Patent document 3) discloses a composition superior in storage stability in a sealed condition. However, this composition disclosed requires the use of a polymer prepared by modifying the end of an organopolysiloxane with an alkoxysilyl alkylene group. That is, due to the preparation of such polymer, this composition has a problem of industrially incurring a higher cost. In addition, Japanese Patent No. 4775600 (Patent document 4) has recently proposed improving storage stability by adding a polyhydric alcohol fatty acid ester such as triacetin which is a typical example thereof. However, since these compounds have an insufficient compatibility with siloxanes, there exists a problem that these compounds may bleed out of a cured product after curing, and that the adhesiveness may thus be impaired.

PRIOR ART DOCUMENT

Patent Document

Patent document 1: Japanese Examined Patent Application Publication No. Sho 39-27643
Patent document 2: JP-A-Sho 55-43119
Patent document 3: Japanese Examined Patent Application Publication No. Hei 7-39547
Patent document 4: Japanese Patent No. 4775600

SUMMARY OF THE INVENTION

Problem to be Solved by the Invention

Thus, it is an object of the present invention to provide an organosilicon compound that is capable of improving the storage stability of a room temperature-curable organopolysiloxane composition such as the so-called silicone RTV rubber composition when added thereto, and has a superior compatibility with siloxanes so that the storage stability (curability after long-term storage) of the aforesaid organopolysiloxane composition can be improved without impairing various properties such as the adhesiveness of a cured product (silicone rubber) obtained by curing such organopolysiloxane composition; and a method for producing the organosilicon compound.

Means to Solve the Problem

The inventors diligently conducted a series of studies to achieve the above objectives, and completed the invention as follows. That is, the inventors found that the organosilicon compound below was useful in solving the aforementioned problems.

Specifically, the present invention is to provide the following organosilicon compound and a method for producing the same.

[1]
An organosilicon compound having, in one molecule, at least one carboxylic acid ester group represented by the following general formula (1) and at least one hydrolyzable silyl group represented by the following general formula (2):

$$-OC(=O)CH_2R^1 \quad (1)$$

wherein $R^1$ represents a hydrogen atom or a methyl group;

$$-SiR^2_{3-n}Y_n \quad (2)$$

wherein $R^2$ represents a substituted or unsubstituted monovalent hydrocarbon group having 1 to 12 carbon atoms, Y represents a hydrolyzable group, and n represents an integer satisfying $1 \leq n \leq 3$.

[2]

The organosilicon compound according to [1], wherein the organosilicon compound is represented by the following general formula (3):

$$Y_n R^2_{3-n}Si-(CH_2)_p-O-R^4-[O-(=O)CH_2R^1]_m \quad (3)$$

wherein $R^4$ represents an m+1 valent hydrocarbon group having 1 to 12 carbon atoms; $R^1$, $R^2$ and Y are defined as above; p represents a number of 2 to 4; m represents a number of 2 to 6; and n is defined as above.

[3]

The organosilicon compound according to [2], wherein $R^4$ represents a hydrocarbon group having 3 to 5 carbon atoms.

[4]

The organosilicon compound according to any one of [1] to [3], wherein $R^1$ represents a hydrogen atom.

[5]

The organosilicon compound according to any one of [1] to [4], wherein the organosilicon compound is an organosilane compound.

[6]

The organosilicon compound according to [5], wherein the organosilicon compound is an organosilane compound having, in one molecule, two or three carboxylic acid ester groups represented by the general formula (1) and one hydrolyzable silyl group represented by the general formula (2).

[7]

The organosilicon compound according to any one of [1] to [6], wherein the organosilicon compound is represented by any one of the following formulae (A) to (D):

[Chemical formulae 1]

(A)

$(H_3CO)_3Si\!\!\diagdown\!\!\diagdown\!\!\diagdown\!\!O\!\!\diagdown\!\!\diagdown\!\!O\!\!\diagdown\!\!$ with acetate groups (B)

$(H_3CO)_3Si\!\!\diagdown\!\!\diagdown\!\!\diagdown\!\!O\!\!\diagdown\!\!$ with three acetate groups (C)

$(C_2H_5O)_3Si\!\!\diagdown\!\!\diagdown\!\!\diagdown\!\!O\!\!\diagdown\!\!\diagdown\!\!O\!\!\diagdown\!\!$ with acetate groups (D)

$(C_2H_5O)_3Si\!\!\diagdown\!\!\diagdown\!\!\diagdown\!\!O\!\!\diagdown\!\!$ with three acetate groups

[8]

The organosilicon compound according to any one of [1] to [7], wherein the organosilicon compound is a storage stabilizer for a room temperature-curable organopolysiloxane composition.

[9]

A method for producing the organosilicon compound as set forth in any one of [1] to [8], comprising:

subjecting a compound and an organosilicon compound to a hydrosilylation reaction under the presence of a platinum compound-containing catalyst, the compound being a compound with one hydroxyl group in a polyhydric alcohol having at least three hydroxyl groups in one molecule being etherified by an alkenyl group having 2 to 4 carbon atoms, and with all the other hydroxyl groups therein being carboxylic acid esterified; and the organosilicon compound being represented by the following formula (4)

$$HSiR^2_{3-n}Y_n \quad (4)$$

wherein $R^2$ represents a substituted or unsubstituted monovalent hydrocarbon group having 1 to 12 carbon atoms, Y represents a hydrolyzable group, and n represents an integer satisfying $1 \leq n \leq 3$.

[10]

The method for producing the organosilicon compound according to [9], wherein the polyhydric alcohol is glycerin or pentaerythritol.

[11]

The method for producing the organosilicon compound according to [9] or [10], wherein being carboxylic acid esterified is being acetic acid esterified.

[12]

The method for producing the organosilicon compound according to any one of [9] to [11], wherein the organosilicon compound is an organosilane compound.

Effects of the Invention

The organosilicon compound of the present invention has an effect of significantly improving the storage stability (curability after long-term storage) of a room temperature-curable organopolysiloxane composition such as the silicone RTV rubber composition without impairing various properties as the adhesiveness of a cured product (silicone rubber) of the aforesaid composition to various base materials.

MODE FOR CARRYING OUT THE INVENTION

The present invention is described in greater detail hereunder.

The organosilicon compound of the present invention is an organosilicon compound such as an organosilane compound having, in one molecule, at least one carboxylic acid ester group represented by the following general formula (1) and at least one hydrolyzable silyl group represented by the following general formula (2).

—OC(=O)CH$_2$R$^1$ (1)

(In the above formula, R$^1$ represents a hydrogen atom or a methyl group.)

—SiR$^2$$_{3-n}$Y$_n$ (2)

(In the above formula, R$^2$ represents a substituted or unsubstituted monovalent hydrocarbon group having 1 to 12 carbon atoms; Y represents a hydrolyzable group; and n represents an integer satisfying 1≤n≤3.)

Here, in the above general formula (1), R$^1$ represents a hydrogen atom or a methyl group (i.e. acetate ester group or propionate ester group as —OC(=O)CH$_2$R$^1$). Here, in order to achieve an adequate effect(s) with a small additive amount, a low-molecular weight substituent group is preferred, and a hydrogen atom is thus particularly preferred. That is, as the above carboxylic acid ester group, an acetate ester group is the most preferred.

Next, in the above general formula (2), examples of the substituted or unsubstituted monovalent hydrocarbon group having 1 to 12 carbon atoms, as represented by R$^2$, include alkyl groups such as a methyl group, an ethyl group, a propyl group, an isopropyl group, a butyl group, an isobutyl group, a tert-butyl group, a pentyl group, a hexyl group, a heptyl group, an octyl group, a nonyl group, a decyl group and a dodecyl group; cycloalkyl groups such as a cyclopentyl group and a cyclohexyl group; alkenyl groups such as a vinyl group, an allyl group, a propenyl group, an isopropenyl group, a butenyl group, a pentenyl group and a hexenyl group; aryl groups such as a phenyl group, a tolyl group, a xylyl group and α-, β-naphthyl group; aralkyl groups such as a benzyl group, 2-phenylethyl group and 3-phenylpropyl group; or groups prepared by substituting a part of or all the hydrogen atoms in any of these groups with, for example, a cyano group and/or halogen atoms such as F, Cl and Br, examples of such substituted groups being 3-chloropropyl group, 3,3,3-trifluoropropyl group and 2-cyanoethyl group. Among the above examples, preferred are alkyl groups such as a methyl group and an ethyl group, and particularly preferred is a methyl group.

Further, in the above general formula (2), Y represents a hydrolyzable group, examples of which include alkoxy groups each having 1 to 4 carbon atoms, such as a methoxy group, an ethoxy group, a propoxy group, an isopropoxy group, a butoxy group, an isobutoxy group and a tert-butoxy group; alkoxyalkoxy groups each having 2 to 4 carbon atoms, such as a methoxyethoxy group, an ethoxyethoxy group and a methoxypropoxy group; acyloxy groups each having 2 to 8 carbon atoms, such as an acetoxy group, an octanoyloxy group and a benzoyloxy group; alkenyloxy groups each having 2 to 6 carbon atoms, such as a vinyloxy group, a propenyloxy group, an isopropenyloxy group and 1-ethyl-2-methylvinyloxy group; ketoxime groups each having 3 to 7 carbon atoms, such as a dimethylketoxime group, a methylethylketoxime group and a diethylketoxime group; amino groups each having 2 to 6 carbon atoms, such as a dimethylamino group, a diethylamino group, a butylamino group and a cyclohexylamino group; aminoxy groups each having 2 to 6 carbon atoms, such as a dimethylaminoxy group and a diethylaminoxy group; and amide groups each having 3 to 8 carbon atoms, such as N-methylacetamide group, N-ethylacetamide group and N-methylbenzamide group. Among these examples, alkoxy groups are more preferred; and lower alkoxy groups each having 1 to 2 carbon atoms, such as a methoxy group and an ethoxy group, are particularly preferred. n represents an integer satisfying 0≤n≤3 (i.e. 0, 1, 2 or 3), preferably an integer of 1 to 3, more preferably 2 or 3, and even more preferably 3.

As a preferable example of the organosilicon compound of the present invention, there may be used an organosilicon compound represented by the following general formula (3).

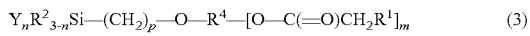
Y$_n$R$^2$$_{3-n}$Si—(CH$_2$)$_p$—O—R$^4$—[O—C(=O)CH$_2$R$^1$]$_m$ (3)

(In the above formula, R$^4$ represents an "m+1" valent hydrocarbon group having 1 to 12 carbon atoms; R$^1$, R$^2$ and Y are defined as above; p represents a number of 2 to 4; m represents a number of 2 to 6; n is defined as above.)

In the general formula (3), examples of the hydrocarbon group represented by R$^4$ include groups obtained by eliminating m hydrogen atoms from any of the monovalent hydrocarbon groups represented by R$^2$. Among such groups, hydrocarbon groups each having 3 to 5 carbon atoms are preferred. Specifically, preferred are groups obtained by eliminating m+1 hydrogen atoms from a hydrocarbon such as propane, n-butane, i-butane, t-butane, n-pentane, isopentane and neopentane.

The organosilicon compound of the present invention can, for example, be produced by the following method.

The organosilicon compound of the invention can be produced by subjecting a compound and an organosilicon compound to a hydrosilylation addition reaction under the presence of a platinum compound-containing catalyst.

The compound subjected to such hydrosilylation addition reaction is a compound with one hydroxyl group in a polyhydric alcohol having at least three hydroxyl groups in one molecule being etherified by an alkenyl group having 2 to 4 carbon atoms e.g. allyl group, and with all the other hydroxyl groups therein being carboxylic acid esterified (e.g. tri-acetoxide of pentaerythritol monoallyl ether, and di-acetoxide of 3-allyloxy-1,2-propanediol).

The organosilicon compound subjected to such hydrosilylation addition reaction is, for example, a hydrolyzable group-containing (organo) hydrogensilane represented by the following formula (4).

HSiR$^2$$_{3-n}$Y$_n$ (4)

(In the above formula, R$^2$ represents a substituted or unsubstituted monovalent hydrocarbon group having 1 to 12 carbon atoms; Y represents a hydrolyzable group; n represents an integer satisfying 1≤n≤3.)

Further, the compound with one hydroxyl group in a polyhydric alcohol having at least three hydroxyl groups in one molecule being allyl-etherified, and with all the other hydroxyl groups therein being carboxylic acid esterified, may be obtained by acetoxylating, for example, 3-allyloxy-1,2-propanediol, or a pentaerythritol monoallyl ether synthesized in accordance with a synthesis route disclosed in JP-A-2013-35768.

Preferable and specific examples of the organosilicon compound of the present invention include compounds (A) to (D) represented by the following structural formulae.

[Chemical formulae 2]

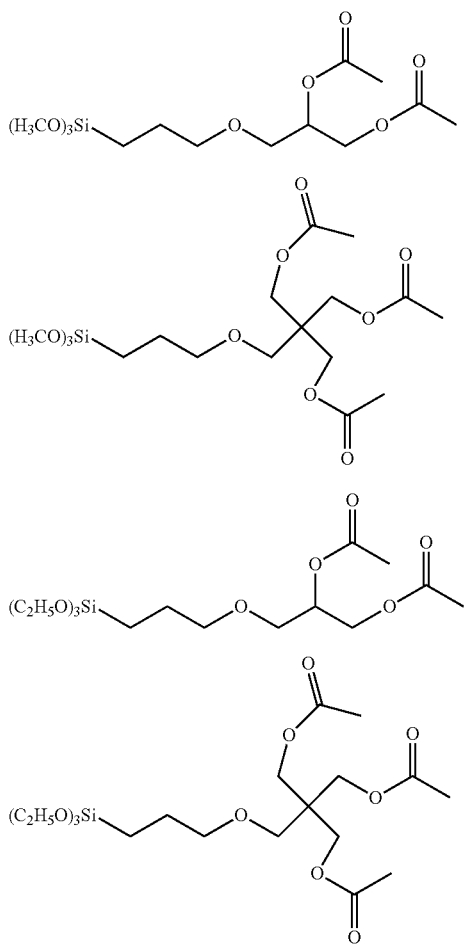

WORKING EXAMPLE

The present invention is described in detail hereunder with reference to working and comparative examples. However, the invention is not limited to the following working examples. Further, in the following examples, "part" refers to "part by mass." Furthermore, a viscosity refers to a value measured by a rotary viscometer at 23° C.

Working Example 1

Synthesis of Organosilicon Compound A

Here, 40.4 g (0.2 mol) of di-acetoxide of 3-allyloxy-1,2-propanediol, 100 mL of toluene and 0.1 g of a toluene solution of a platinum-1,3-divinyl-1,1,3,3-tetramethyldisiloxane complex (product name: PL-50T by Shin-Etsu Chemical Co., Ltd.) were put into a 500 mL separable flask equipped with a stirrer, a reflux condenser, a dropping funnel and a thermometer, followed by spending 30 min delivering thereinto by drops 25.6 g (0.2 mol) of trimethoxysilane at an inner temperature of 75 to 85° C. Later, stirring was performed at 80° C. for an hour. Further, by carrying out vacuum concentration, there was obtained 66.3 g (yield 98%) of the organosilicon compound represented by the above formula (A), as a yellow transparent liquid.

In order to confirm the structure of the product obtained, $^1$H-NMR spectrum measurement was performed.

$^1$H-NMR (CDCl$_3$) δ0.62 (t, 2H), 1.64 (m, 2H), 2.04 (s, 3H), 2.06 (s, 3H), 3.40 (m, 2H), 3.42 (m, 2H), 3.54 (s, 9H), 4.11-4.33 (m, 2H), 5.15 (m, 1H)

Working Example 2

Synthesis of Organosilicon Compound B

Here, 60.4 g (0.2 mol) of tri-acetoxide of pentaerythritol monoallyl ether, 100 mL of toluene and 0.1 g of the toluene solution of the platinum-1,3-divinyl-1,1,3,3-tetramethyldisiloxane complex (product name: PL-50T by Shin-Etsu Chemical Co., Ltd.) were put into a 500 mL separable flask equipped with a stirrer, a reflux condenser, a dropping funnel and a thermometer, followed by spending 30 min delivering thereinto by drops 25.6 g (0.2 mol) of trimethoxysilane at an inner temperature of 75 to 85° C. Later, stirring was performed at 80° C. for an hour. Further, by carrying out vacuum concentration, there was obtained 83.1 g (yield 98%) of the organosilicon compound represented by the above formula (B), as a thin yellow transparent liquid.

In order to confirm the structure of the product obtained, $^1$H-NMR spectrum measurement was performed.

$^1$H-NMR (CDCl$_3$) δ0.58 (t, 2H), 1.59 (m, 2H), 2.00 (s, 9H), 3.32 (t, 2H), 3.36 (s, 2H), 3.52 (s, 9H), 4.08 (s, 6H)

Reference Example 1

Here, homogenously mixed together were 100 parts of a dimethylpolysiloxane with both of its molecular chain ends being blocked by a hydroxyl group, and having a viscosity of 50,000 mPa·s; 50 parts of a dimethylpolysiloxane with both of its molecular chain ends being blocked by a trimethylsilyl group, and having a viscosity of 100 mPa·s; 100 parts of a synthetic calcium carbonate (HAKUENKA CCR by SHIRAISHI CALCIUM KAISHA, LTD.); and 100 parts of an untreated calcium carbonate (SUPER S by Maruo Calcium Co., Ltd.). Next, added to 100 parts of the dimethylpolysiloxane thus prepared were 9 parts of methyltrimethoxysilane; 6 parts of titanium diisopropoxybis (ethylacetoacetate); and 2 parts of the organosilicon compound A synthesized in working example 1, followed by uniformly mixing them under a moisture-blocked condition so as to obtain a one-component dealcoholization-type organopolysiloxane composition 1.

Reference Example 2

A composition 2 was prepared in a manner similar to that of the reference example 1, except that 2 parts of the organosilicon compound B synthesized in working example 2 was added instead of 2 parts of the organosilicon compound A.

Comparative Reference Example 1

A composition 3 was prepared in a manner similar to that of the reference example 1, except that 2 parts of triacetin as a conventional storage stabilizer was added instead of 2 parts of the organosilicon compound A.

Comparative Reference Example 2

A composition 4 was prepared in a manner similar to that of the reference example 1, except that 2 parts of the organosilicon compound A was not added.

Next, a physical property test, a shear adhesion test, and a storage stability test were performed on each composition prepared in reference examples 1 and 2; and comparative reference examples 1 and 2. The results of these tests are shown in Table 1.

Physical Property

Each composition prepared was pushed out into a polyethylene-made frame, followed by curing the same at 23° C., 50% RH for seven days so as to harden the same, thereby obtaining a sheet having a thickness of 2 mm. The physical properties of this sheet were measured in accordance with JIS K 6249.

Shear Adhesion Test

Each composition prepared and an adherend (polycarbonate resin, acrylic resin) having a width of 25 mm and a length of 100 mm were used. The composition was cured at 23° C., 50% RH for seven days so as to obtain a shear adhesion test specimen having an adhesion area of 2.5 cm² and an adhesion thickness of 1 mm. A shear adhesion force thereof was then measured in accordance with JIS K 6249.

Storage Stability

Each composition was put into a polyethylene-made cartridge for sealing material (volume 330 mL), followed by sealing such cartridge with an inner plug. This cartridge was then stored in a drying machine at 70° C. for seven days, followed by taking it out of the drying machine, and measuring the physical properties thereof in a similar manner as above, as post-heating/storage physical properties.

TABLE 1

| | | Reference example 1 | Reference example 2 | Comparative reference example 1 | Comparative reference example 2 |
|---|---|---|---|---|---|
| Physical property | Hardness Duro.A | 27 | 27 | 27 | 28 |
| | Maximum point strength (MPa) | 1.4 | 1.3 | 1.2 | 1.3 |
| | Breaking point elongation percentage (%) | 780 | 650 | 690 | 600 |
| Shear adhesion | Polycarbonate resin (MPa) | 1.0 | 1.0 | 0.2 | 0.8 |
| | Acrylic resin (MPa) | 1.0 | 1.0 | 0.3 | 0.9 |
| Storage stability | Hardness Duro.A | 28 | 24 | 28 | Uncured |
| | Maximum point strength (MPa) | 1.4 | 1.1 | 1.2 | |
| | Breaking point elongation percentage (%) | 660 | 680 | 650 | |

According to the results shown in Table 1, it became clear that the compositions of reference examples 1 and 2 exhibited a favorable storage stability (curability after long-term storage) without impairing the adhesiveness of the cured products (silicone rubbers) thereof, as compared to the corresponding comparative reference examples 1 and 2.

However, the present invention is not limited to the above working examples. The above embodiments are simply given as examples; and any embodiment shall be included in the technical scope of the invention, if the embodiment substantively has a structure identical to the technical idea described in the claims of the present invention and brings about the similar functions and effects.

The invention claimed is:

1. An organosilicon compound of formula (3)

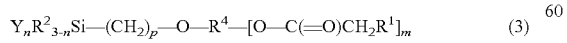

wherein n is 1, 2, or 3, p is a number of 2 to 4, m is a number of 2 to 6, Y is a hydrolyzable group, $R^2$ is an unsubstituted monovalent hydrocarbon group having 1 to 12 carbon atoms, $R^4$ is an m+1 valent hydrocarbon group having 1 to 12 carbon atoms, and $R^1$ is a hydrogen atom or a methyl group, said organosilicon compound having, in one molecule, at least two carboxylic acid ester groups of formula (1) and at least one hydrolyzable silyl group of formula (2):

 (1)

 (2)

wherein $R^1$, $R^2$, n, and Y are as defined above.

2. The organosilicon compound according to claim 1, wherein $R^4$ is a hydrocarbon group having 3 to 5 carbon atoms.

3. The organosilicon compound according to claim 1 wherein $R^1$ is a hydrogen atom.

4. The organosilicon compound according to claim 1, wherein the organosilicon compound is an organosilane compound.

5. The organosilicon compound according to claim 4, wherein the organosilicon compound is an organosilane compound having, in one molecule, two or three carboxylic acid ester groups of formula (1) and one hydrolyzable silyl group of formula (2).

6. The organosilicon compound according to claim 1, wherein the organosilicon compound has any one of the following formulae (A) to (D):

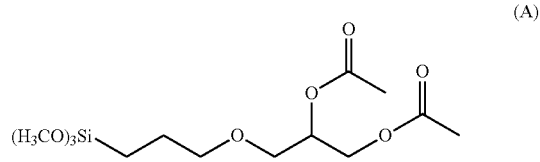

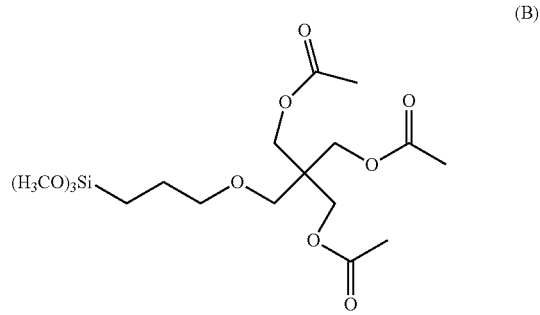

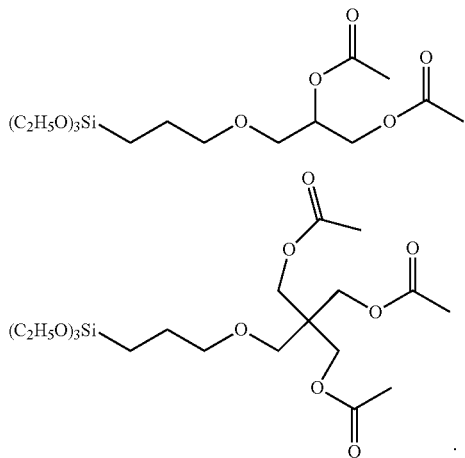

(C)

(D)

7. The organosilicon compound according to claim 1, wherein the organosilicon compound is a storage stabilizer for a room temperature-curable organopolysiloxane composition.

8. A method for producing the organosilicon compound as set forth in claim 1, comprising:
   subjecting a compound and an organosilicon compound to a hydrosilylation reaction under the presence of a platinum compound-containing catalyst,
   the compound being a compound with one hydroxyl group in a polyhydric alcohol having at least three hydroxyl groups in one molecule being esterified by an alkenyl group having 2 to 4 carbon atoms, and with all the other hydroxyl groups therein being carboxylic acid esterified; and
   the organosilicon compound by having the following formula (4)

$$HSiR^2_{3-n}Y_n \qquad (4)$$

wherein $R^2$ is a substituted or unsubstituted monovalent hydrocarbon group having 1 to 12 carbon atoms, Y is a hydrolyzable group, and n is an integer satisfying $1 \leq n \leq 3$.

9. The method for producing the organosilicon compound according to claim 8, wherein the polyhydric alcohol is glycerin or pentaerythritol.

10. The method for producing the organosilicon compound according to claim 8, wherein being carboxylic acid esterified is being acetic acid esterified, and the carboxylic acid ester group of formula (1) is an acetate ester group.

11. The method for producing the organosilicon compound according to claim 8, wherein the organosilicon compound subjected to the hydrosilylation reaction is an organosilane compound.

12. The organosilicon compound according to claim 1, wherein $R^2$ is a methyl group or an ethyl group.

13. The organosilicon compound according to claim 1, wherein the $R^4$ groups are obtained by eliminating m+1 hydrogen atoms from a hydrocarbon selected from the group consisting of propane, n-butane, i-butane, t-butane, n-pentane, isopentane, and neopentane.

14. The organosilicon compound according to claim 1, wherein $R^1$ is a methyl group.

* * * * *